(12) United States Patent
Dobrinsky et al.

(10) Patent No.: US 9,687,577 B2
(45) Date of Patent: Jun. 27, 2017

(54) ULTRAVIOLET ILLUMINATOR FOR FOOTWEAR TREATMENT

(71) Applicant: Sensor Electronic Technology, Inc., Columbia, SC (US)

(72) Inventors: Alexander Dobrinsky, Loudonville, NY (US); Michael Shur, Latham, NY (US); Remigijus Gaska, Columbia, SC (US)

(73) Assignee: Sensor Electronic Technology, Inc., Columbia ( * ) Notice: Subject to any disclaimer, the term of this patent is extended or adjusted under 35 U.S.C. 154(b) by 0 days.

(21) Appl. No.: 14/853,036

(22) Filed: Sep. 14, 2015

(65) Prior Publication Data

US 2016/0074547 A1  Mar. 17, 2016

Related U.S. Application Data

(60) Provisional application No. 62/050,126, filed on Sep. 13, 2014, provisional application No. 62/050,127, filed on Sep. 13, 2014, provisional application No. 62/050,322, filed on Sep. 15, 2014.

(51) Int. Cl.
    *A61L 2/10*   (2006.01)
(52) U.S. Cl.
    CPC ............ *A61L 2/10* (2013.01); *A61L 2202/14* (2013.01)
(58) Field of Classification Search
    CPC ......................................................... A61L 2/10
    USPC ............... 250/453.11, 454.11, 455.11, 493.1, 250/504 R; 422/22, 24
    See application file for complete search history.

(56) References Cited

U.S. PATENT DOCUMENTS

| 4,045,119 | A  | 8/1977  | Eastgate       |
| 5,675,689 | A  | 10/1997 | Nath           |
| 6,163,641 | A  | 12/2000 | Eastgate       |
| 6,314,227 | B1 | 11/2001 | Nath           |
| 6,418,257 | B1 | 7/2002  | Nath           |
| 6,476,409 | B2 | 11/2002 | Iwasaki et al. |
| 6,773,584 | B2 | 8/2004  | Saccomanno     |
| 6,863,428 | B2 | 3/2005  | Lundin         |
| 6,936,854 | B2 | 8/2005  | Iwasaki et al. |
| 7,016,566 | B2 | 3/2006  | Dimas et al.   |
| 7,211,763 | B2 | 5/2007  | Zhang          |

(Continued)

FOREIGN PATENT DOCUMENTS

WO    2005011753 A1    2/2005

OTHER PUBLICATIONS

Agilent Technologies, "Light Guide Techniques Using LED Lamps, Application Brief I-003," 2001, 22 pages.

(Continued)

*Primary Examiner* — Nicole Ippolito
(74) *Attorney, Agent, or Firm* — Labatt, LLC

(57) ABSTRACT

An ultraviolet (UV) footwear illuminator for footwear treatment is disclosed. In one embodiment, the UV footwear illuminator includes an insert adapted for placement in an article of footwear. At least one UV radiation source is located in the insert and is configured to emit UV radiation in the footwear through a transparent window region formed in the insert. A control unit is configured to control at least one predetermined UV radiation characteristics associated with the radiation emitted from each UV radiation source. A power supply is configured to power each UV radiation source and the control unit.

20 Claims, 10 Drawing Sheets

(56) References Cited

U.S. PATENT DOCUMENTS

| | | |
|---|---|---|
| 7,553,456 B2 | 6/2009 | Gaska et al. |
| 7,613,378 B2 | 11/2009 | Girardon et al. |
| 7,634,996 B2 | 12/2009 | Gaska et al. |
| 7,660,509 B2 | 2/2010 | Bryan et al. |
| 7,914,852 B2 | 3/2011 | Belz et al. |
| 7,960,706 B2 | 6/2011 | Ullman |
| 8,177,383 B2 | 5/2012 | Reuben |
| 8,277,734 B2 | 10/2012 | Koudymov et al. |
| 8,434,909 B2 | 5/2013 | Nichol et al. |
| 8,442,602 B2 | 5/2013 | Wong et al. |
| 8,980,178 B2 | 3/2015 | Gaska et al. |
| 9,006,680 B2 | 4/2015 | Bettles et al. |
| 9,138,499 B2 | 9/2015 | Bettles et al. |
| 2003/0044149 A1 | 3/2003 | Fraval et al. |
| 2004/0036560 A1 | 2/2004 | Higuchi et al. |
| 2006/0002675 A1 | 1/2006 | Choi et al. |
| 2009/0034236 A1 | 2/2009 | Reuben |
| 2010/0014027 A1 | 1/2010 | Li et al. |
| 2010/0165621 A1 | 7/2010 | Hoffend, Jr. et al. |
| 2011/0149201 A1 | 6/2011 | Powell et al. |
| 2011/0273906 A1 | 11/2011 | Nichol et al. |
| 2011/0286222 A1 | 11/2011 | Coleman |
| 2011/0309032 A1 | 12/2011 | Makl |
| 2013/0048545 A1 | 2/2013 | Shatalov et al. |
| 2013/0106918 A1 | 5/2013 | Bita et al. |
| 2013/0270445 A1 | 10/2013 | Gaska et al. |
| 2013/0336839 A1* | 12/2013 | Gil .................. A61L 2/10 422/24 |
| 2014/0001374 A1* | 1/2014 | Ullman .............. A61L 2/088 250/428 |
| 2014/0060094 A1 | 3/2014 | Shur et al. |
| 2014/0060095 A1 | 3/2014 | Shur et al. |
| 2014/0060096 A1 | 3/2014 | Shur et al. |
| 2014/0060104 A1 | 3/2014 | Shur et al. |
| 2014/0061509 A1 | 3/2014 | Shur et al. |
| 2014/0071142 A1 | 3/2014 | Steyn |
| 2014/0202962 A1 | 7/2014 | Bilenko et al. |
| 2014/0373606 A1 | 12/2014 | Kraiczek et al. |
| 2015/0008167 A1 | 1/2015 | Shturm et al. |
| 2015/0069265 A1 | 3/2015 | Smetona et al. |
| 2015/0069270 A1 | 3/2015 | Shur et al. |
| 2015/0091043 A1 | 4/2015 | Shur et al. |
| 2015/0165079 A1 | 6/2015 | Shur et al. |
| 2015/0217011 A1 | 8/2015 | Bettles et al. |
| 2015/0238645 A1 | 8/2015 | Agafonov et al. |
| 2015/0297767 A1 | 10/2015 | Gaska et al. |
| 2015/0336810 A1 | 11/2015 | Smetona et al. |
| 2015/0360606 A1* | 12/2015 | Thompson ........ B60Q 3/0283 362/490 |
| 2016/0000953 A1 | 1/2016 | Bettles et al. |
| 2016/0058020 A1 | 3/2016 | Shur et al. |
| 2016/0106873 A1 | 4/2016 | Dobrinsky et al. |
| 2016/0114067 A1 | 4/2016 | Dobrinsky et al. |
| 2016/0114186 A1 | 4/2016 | Dobrinsky et al. |
| 2016/0128526 A1 | 5/2016 | Dobrinsky et al. |

OTHER PUBLICATIONS

Dupont, "Amorphous Fluoroplastic Resin," www.teflon.com/industrial, 2013, 4 pages.

Gore® Diffuse Reflector Product, printed from http://www.gore.com/en_xx/products/electronic/specialty/specialty.html?RDCT=gore.com on Sep. 5, 2014.

Joo, B., et al., "Design guidance of backlight optic for improvement of the brightness in the conventional edge-lit LCD backlight," 2010, 6 pages.

Li, C., et al., "Prism-pattern design of an LCD light guide plate using a neural-network optical model," 2010, 5 pages.

Yang, M., et al., "Optical properties of Teflon AF amorphous fluoropolymers," Jul.-Sep. 2008, 9 pages.

Colombe, Y., et al., "Single-mode optical fiber for high-power, low-loss UV transmission," Optics Express, Aug. 2014, p. 19783, vol. 22, No. 16.

Fevrier, S., et al., "Ultraviolet guiding hollow-core photonic crystal fiber," 2009, 2888-2890, Opt. Lett.34(19)X.

Gebert, F., et al., "Damage-free single-mode transmission of deep-UV light in hollow-core PCF," Optics Express, Jun. 2014, p. 15388, vol. 22, No. 13.

Gonschior, C. P., et al. "Characterization of UV single-mode and low-mode fibers," 2010, Proc. of SPIE vol. 7559 75590X-1.

Yamamoto, N., "Single-mode delivery of 250 nm light using a large mode area photonic crystal fiber," 2009, p. 16933-16940, Opt. Express17(19).

Bedtelyon, J., U.S. Appl. No. 14/853,014, Office Action1, Jul. 1, 2016, 19 pages.

Deo, D., U.S. Appl. No. 14/853,057, Office Action1, Jul. 21, 2016, 21 pages.

Bedtelyon, J., U.S. Appl. No. 14/853,014, Notice of Allowance, Nov. 21, 2016, 13 pages.

Kang, S. International Application No. US2015/049917, International Search Report and Written Opinion, Dec. 23, 2015, 13 pages.

International Application No. US2015/049922, International Search Report and Written Opinion, Mar. 18, 2016, 14 pages.

Deo, D., U.S. Appl. No. 14/853,057, Notice of Allowance, Dec. 28, 2016, 15 pages.

Martin, et al., "Ordered arrays of polymeric nanopores by using inverse nanostructured PTFE surfaces," 2012, 10 pages, IOP Publishing.

Deo, D., U.S. Appl. No. 14/853,057, Notice of Allowance, Mar. 1, 2017, 9 pages.

Bedtelyon, J., U.S. Appl. No. 14/853,014, Notice of Allowance, Feb. 28, 2017, 5 pages.

* cited by examiner

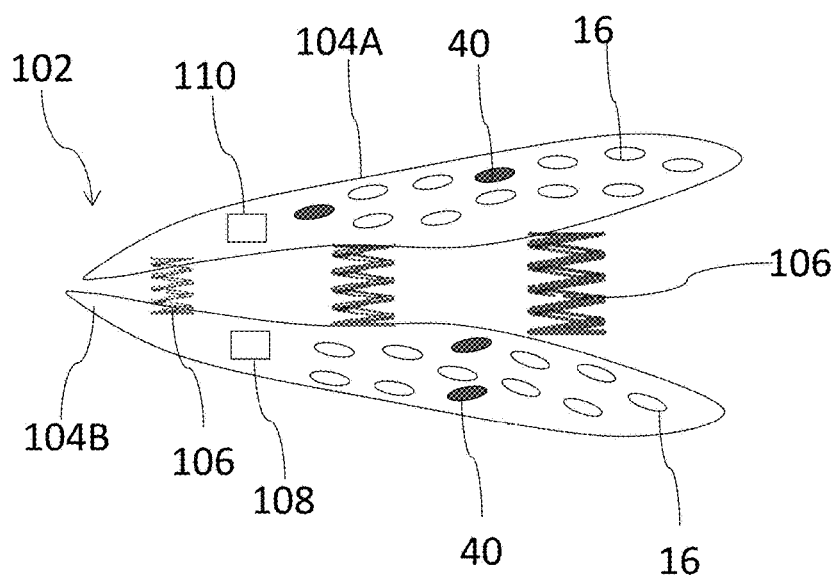
FIG. 11
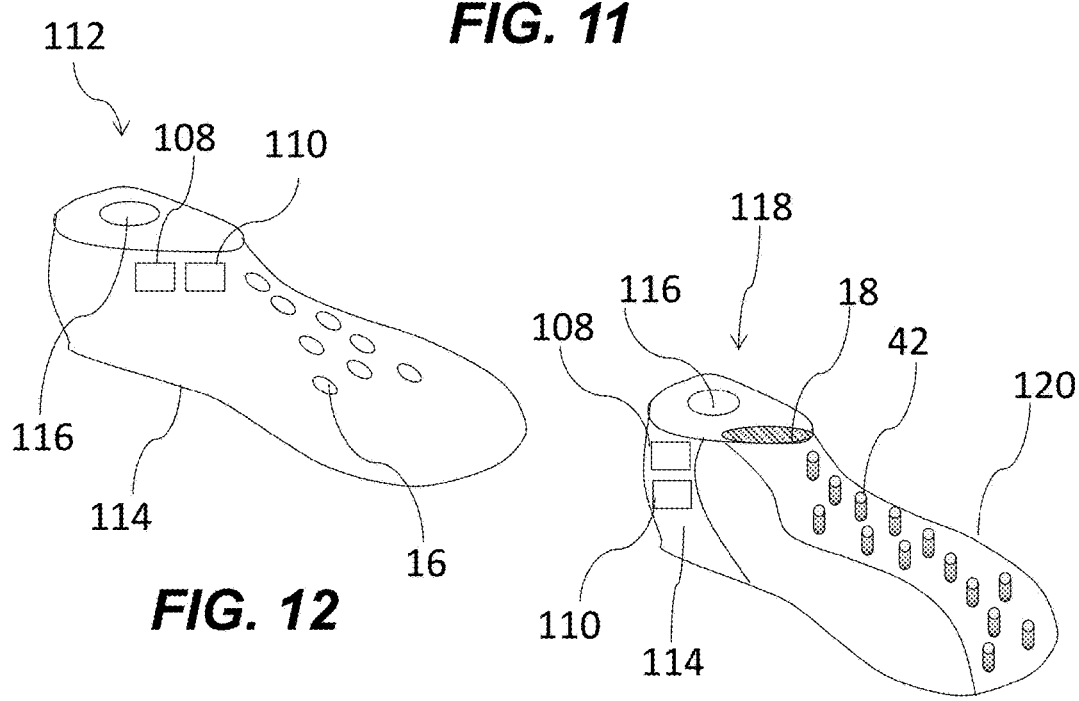
FIG. 12
FIG. 13

ULTRAVIOLET ILLUMINATOR FOR FOOTWEAR TREATMENT

REFERENCE TO RELATED APPLICATIONS

The present patent application claims the benefit of: U.S. Provisional Application No. 62/050,126, which was filed on 13 Sep. 2014; U.S. Provisional Application No. 62/050,127, which was filed on 13 Sep. 2014; and U.S. Provisional Application No. 62/050,322, which was filed on 15 Sep. 2014, each of which is hereby incorporated by reference. Aspects of the invention described herein are related to U.S. patent application Ser. No. 14/478,266, which was filed on 5 Sep. 2014 and U.S. patent application Ser. No. 14/630,692, which was filed on 25 Feb. 2015, each of which is hereby incorporated by reference.

TECHNICAL FIELD

The disclosure relates generally to footwear treatment, and more particularly, to using ultraviolet (UV) radiation for purposes of disinfection, sterilization, and/or sanitization of an article of footwear and medical treatment to a foot of a wearer of the footwear.

BACKGROUND ART

The environment inside articles of footwear such as, for example, shoes, provides favorable conditions for the growth of infectious biological microorganisms, allowing bacteria, viruses, fungi, and other associated odors to proliferate. For example, foot perspiration within shoes promotes warmth and dampness. The excessive levels of harmful microorganisms sustained in enclosed shoes may cause or promote various foot maladies. It is well known that exposure to ultraviolet (UV) light of certain wavelengths, intensities, and durations can destroy or inhibit growth of surface pathogens. One approach to treating a shoe includes disinfecting the shoe with UV light generated from UV light emitting diodes (LEDs) that are mounted over an inside of a hollow shoe tree that is inserted into the toe of the shoe. UV LEDs that emit light within a germicidal range can be used to destroy microorganisms residing in the shoe. Another approach includes using an alternative light source such as a UV germicidal bulb in place of the UV LEDs. A third approach includes using visible light LEDs or a visible light source, both of which are less expensive and easier to acquire than a UV germicidal light source. Visible light LEDs or visible light bulbs can be used because light within the visible spectrum inhibits or prevents further growth of microorganisms as opposed to actually killing them. Another approach which is suitable for commercial purposes, relies on using an enclosure to contain UV light emanating from a bulb inserted inside a shoe without the support of a shoe tree.

All of the aforementioned approaches can be implemented with safeguards to contain the UV radiation exposure within a region of interest. For example, an opaque or a translucent barrier can be placed between the propagation path of the UV radiation and any openings in the shoe. One type of a barrier is a seal set around the spine or heel of a shoe tree that is placed in the shoe. Another barrier includes a light restrictor or caps incorporated in the forepart of a shoe tree that are placed over any openings in the shoe. Another approach of preventing unwanted UV exposure entails activating the UV light source only if a threshold level of ambient light is not detected. Ambient light detected inside a shoe indicates a light leak, which could allow UV radiation to escape. A light leak could be the result of improper insertion of the UV light source into the shoe. Disabling the UV light source when a threshold level of ambient light is detected by a light sensor, such as a photodiode or a phototransistor, prevents unwanted UV exposure.

SUMMARY OF THE INVENTION

Aspects of the present invention provide a solution for footwear treatment of an article of footwear with ultraviolet (UV) radiation.

A first aspect of the present invention provides an ultraviolet (UV) footwear illuminator. The UV footwear illuminator comprises: an insert adapted for placement in an article of footwear; at least one UV radiation source located in the insert configured to emit UV radiation in the footwear through a transparent window region formed in the insert; a control unit configured to control at least one of a plurality of predetermined UV radiation characteristics associated with the radiation emitted from each UV radiation source; and a power supply configured to power each UV radiation source and the control unit.

A second aspect of the present invention provides a UV footwear treatment system. The UV footwear treatment system comprises: an insert adapted for placement in an article of footwear; at least one UV radiation source enclosed in the insert configured to emit UV radiation in the footwear through a transparent window region formed in the insert; and a wave guiding structure configured to distribute the UV radiation generated from each UV radiation source throughout the footwear.

A third aspect of the present invention provides an article of footwear. The article of footwear comprises an insole insert having at least one UV radiation source located therein configured to emit UV radiation in the footwear through a transparent window region; a wave guiding structure configured to distribute the UV radiation generation from each UV radiation source throughout the footwear; at least one footwear condition sensor located in the insert, each sensor configured to generate a footwear condition signal representative of an operational condition; and a control unit configured to control operation of the at least one UV radiation source and the at least one footwear condition sensor.

The illustrative aspects of the present invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the present invention.

FIG. 11 shows a shoe tree according to an embodiment of the present invention;

FIG. 12 shows a shoe tree according to another embodiment of the present invention;

FIG. 13 shows a shoe tree according to still another embodiment of the present invention.

It is noted that the drawings may not be to scale. The drawings are intended to depict only typical aspects of the present invention, and therefore should not be considered as limiting the scope of the present invention. In the drawings, like numbering represents like elements between the drawings.

DETAILED DESCRIPTION OF THE INVENTION

As indicated above, aspects of the present invention are directed to a solution for footwear treatment of an article of footwear with ultraviolet (UV) radiation. The solution for footwear treatment can include any now known or later developed approach that incorporates the concepts of the various embodiments described herein. As used herein, footwear treatment can entail sanitizing, disinfecting, and/or sterilizing an article of footwear. Sanitizing generally means reducing the number of bacterial contaminants to a predetermined safe level. Disinfecting generally means destroying pathogenic and other types of microorganisms, while sterilizing is more extensive in that kills all microbial forms. Articles of footwear of which the various embodiments of the present invention can be applied for use therewith can include a wide variety of footwear. Examples include, but are not limited to, sneakers, shoes, boots, high heels, slippers, sandals, flip-flops, cleats, and medical walking boots and braces.

UV radiation, which can be used interchangeably with UV light, means electromagnetic radiation having a wavelength ranging from approximately 10 nanometers (nm) to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

As used herein, a layer is transparent when it allows at least ten percent of radiation having a target wavelength, which is radiated at a normal incidence to an interface of the layer, to pass there through. A layer is highly transparent when the layer allows at least thirty percent of the radiation to pass there through, and a layer is substantially transparent when the layer allows at least eighty percent of the radiation to pass there through. Furthermore, as used herein, a layer is a reflective layer when the layer reflects at least ten percent of radiation having a target wavelength, which is radiated at a normal incidence to an interface of the layer and is highly reflective when the layer reflects at least eighty percent of the radiation. It is understood that a layer can be both transparent and reflective. The target wavelength of the radiation can correspond to a wavelength of radiation emitted or sensed (e.g., peak wavelength +/−five nanometers) by an active region of an optoelectronic device during operation thereof. For a given layer, the wavelength can be measured in a material of consideration and can depend on a refractive index of the material.

Figure 1A:
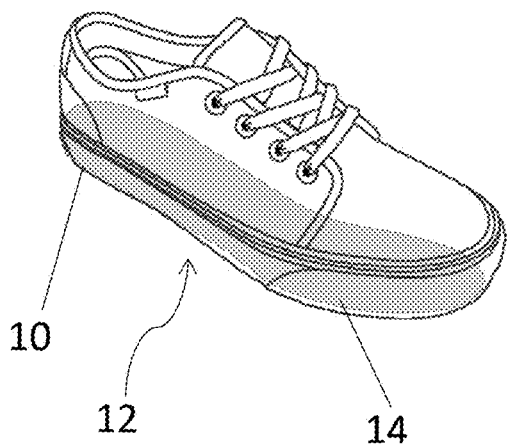
FIGS. 1A-1B show an ultraviolet (UV) footwear illuminator according to one embodiment of the present invention.
Figure 1B:
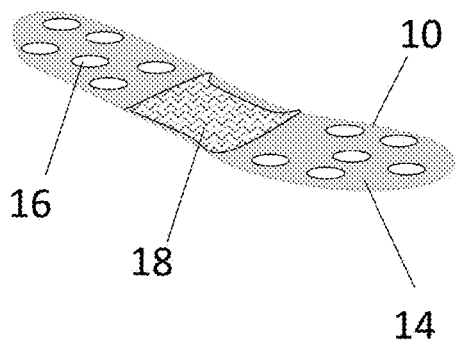

Turning to the drawings, FIGS. 1A-1B show a UV footwear illuminator 10 according to one embodiment of the present invention. In particular, FIG. 1A shows the UV footwear illuminator 10 in use with an article of footwear illustrated as a shoe 12, such as a sneaker. The UV footwear illuminator 10 includes an insert 14 adapted for placement in the shoe 12. The insert 14 can take the form of an insole, a footbed enclosure, and/or the like that is adapted for insertion into the interior of the shoe 12. In one embodiment the insert 14 can be permanently affixed or integrated with the shoe 12. In another embodiment, the insert 14 can be used in place of an insole that is provided with the shoe, and removed and inserted as desired. For example, the insert 14 in this embodiment could take the form of a removable insole, footbed enclosure, foot cushion, orthotic and/or the like.

FIG. 1B shows a more detailed view of the UV footwear illuminator 10 and the insert 14. As shown in FIG. 1B, at least one UV radiation source 16 is located in the insert 14. The set of UV radiation sources 16 illustrated in FIGS. 1A-1B can be located on the top and/or the bottom surfaces of the insert 14. For example, since the embodiment of FIGS. 1A-1B is directed to footwear such as a shoe, the set of UV radiation sources 16 can be located on any of the surfaces of the insert 14.

Each UV radiation source 16 is configured to emit UV radiation in the shoe 12 when placed therein. The set of UV radiation sources 16 shown in FIG. 1 can comprise any combination of one or more UV radiation emitters. Examples of UV radiation emitters can include, but are not limited to, high intensity UV lamps (e.g., high intensity mercury lamps), discharge lamps, UV light emitting diodes (LEDs), super luminescent LEDs, laser diodes, and/or the like. In one embodiment, the set of UV radiation sources 16 can include a set of LEDs manufactured with one or more layers of materials selected from the group-III nitride material system (e.g., $Al_xIn_yGa_{1-X-Y}N$, where $0 \le x$, $y \le 1$, and $x+y \le 1$ and/or alloys thereof).

Figure 6:
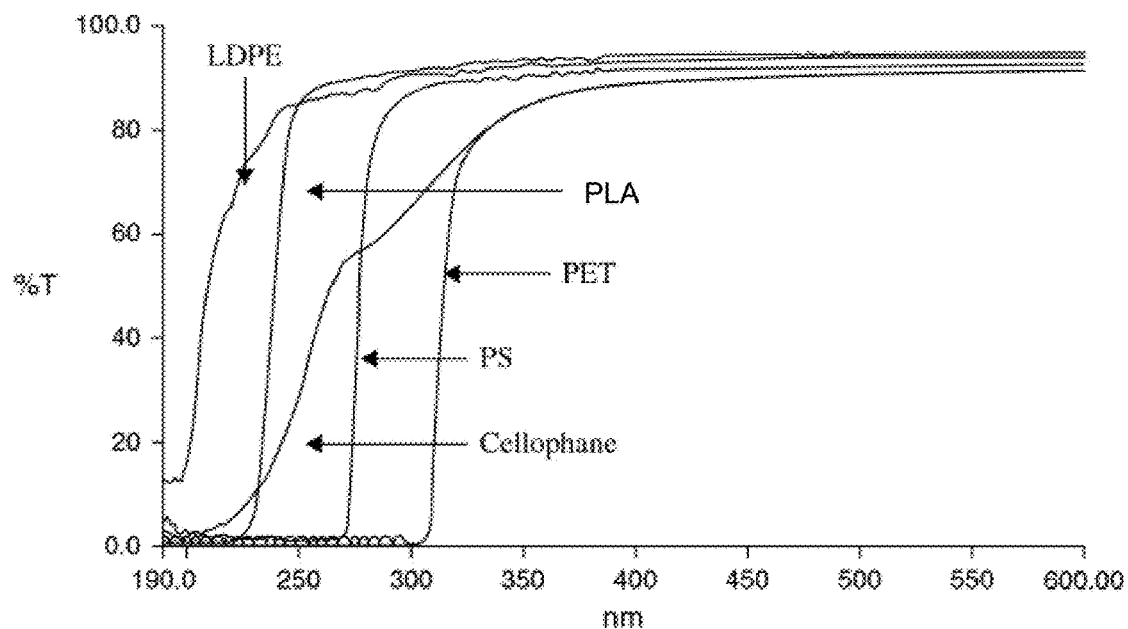
FIG. 6 shows a graph comparing the transmission properties of various UV transparent fluoropolymer materials that can be used in components described in the various embodiments of the present invention.

Although not shown in FIG. 1B, the UV radiation sources 16 can include a transparent window region through which the UV radiation emitted from the radiation sources passes towards a surface of the insert 14. This transparent window region can be formed of any UV transparent material, such as a UV transparent fluoropolymer, such as fluorinated ethylene propylene co-polymer (EFEP), fluorinated ethylene propylene (FEP), polytetrafluoroethylene (PTFE), ethylene chlorotrifluoroethylene (ECTFE), polychlorotrifluoroethylene (PCTFE), perfluoroalkoxy (PFA), polyvinylidene fluoride (PVDF), ethylene tetrafluoroethylene (ETFE), tetrafluoroethylene hexafluoropropylene vinylidene fluoride co-polymer (THV), low density polyethylene (LDPE), perfluoro methyl alkoxy (MFA), and/or the like. While primarily described in conjunction with fluoropolymers, it is understood that other comparable materials can be utilized for the transparent window region. Illustrative materials include polylactide (PLA), fused silica, sapphire, THE, and/or the like. FIG. 6 shows a graph comparing the transmission properties of some of the above-listed UV transparent fluoropolymer materials.

In operation, the set of UV radiation sources 16 can function in a coordinated manner. For example, the UV radiation sources 16 can operate at the same wavelengths and intensities for the same duration, or the sources can operate at different wavelengths and intensity for varying durations. In one embodiment, a first set of UV radiation sources 16 can operate at a target wavelength and intensity that is designed for the disinfection of bacteria and/or viruses within the shoe 12, while a second set of UV radiation sources can operate at a different target wavelength and intensity that is designed for the medical treatment of the skin of a foot that is to be placed in the shoe.

FIG. 1B further shows that the UV footwear illuminator 10 can include a wave guiding structure 18 in the insert 16 that is configured to direct and/or deliver UV radiation that is emitted from the UV radiation sources 16 to a particular location/area within the shoe 12, in a particular direction and pattern. Examples of a wave guiding structure can include, but are not limited to, a waveguide, UV fibers each terminating at an opening, a diffuser, and/or the like. An approach for forming waveguides using UV transparent fluoropolymers is described in U.S. Provisional Application No. 62/050,126. Further details of the wave guiding structure 18 used herein are described below.

Figure 2A:
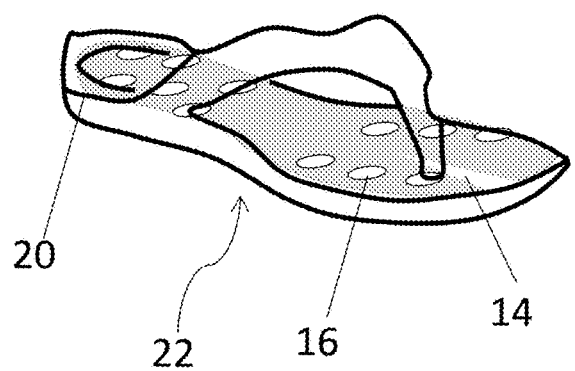
FIGS. 2A-2B show an UV footwear illuminator according to another embodiment of the present invention.
Figure 2B:
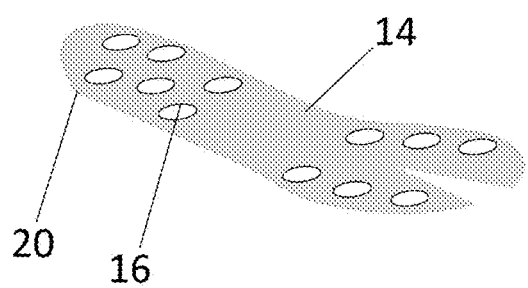

FIGS. 2A-2B show a UV footwear illuminator 20 according to another embodiment of the present invention. In particular, FIG. 2A shows the UV footwear illuminator 20 in use with an article of footwear illustrated as a sandal 22. The UV footwear illuminator 20 includes an insert 14 adapted for placement with the sandal 22. The insert 14 can take the form of an insole, a footbed enclosure, and/or the like that is inserted into the interior of the sandal 22. In the embodiment illustrated in FIGS. 2A-2B, the UV footwear illuminator 20 includes at least one UV radiation source 16. The set of UV radiation sources 16 illustrated in FIGS. 2A-2B can be located on the top and/or the bottom surfaces of the insert 14. Since the article of footwear in this embodiment is a sandal, the set of UV radiation sources 16 can be placed primarily on the bottom surface of the insert 14. Although the insert 14 of the UV footwear illuminator 20 shown in FIGS. 2A-2B does not include a wave guiding structure 18, those skilled in the art will appreciate that one like that shown in FIG. 1B can be deployed with footwear such as the sandal 22.

Figure 3:
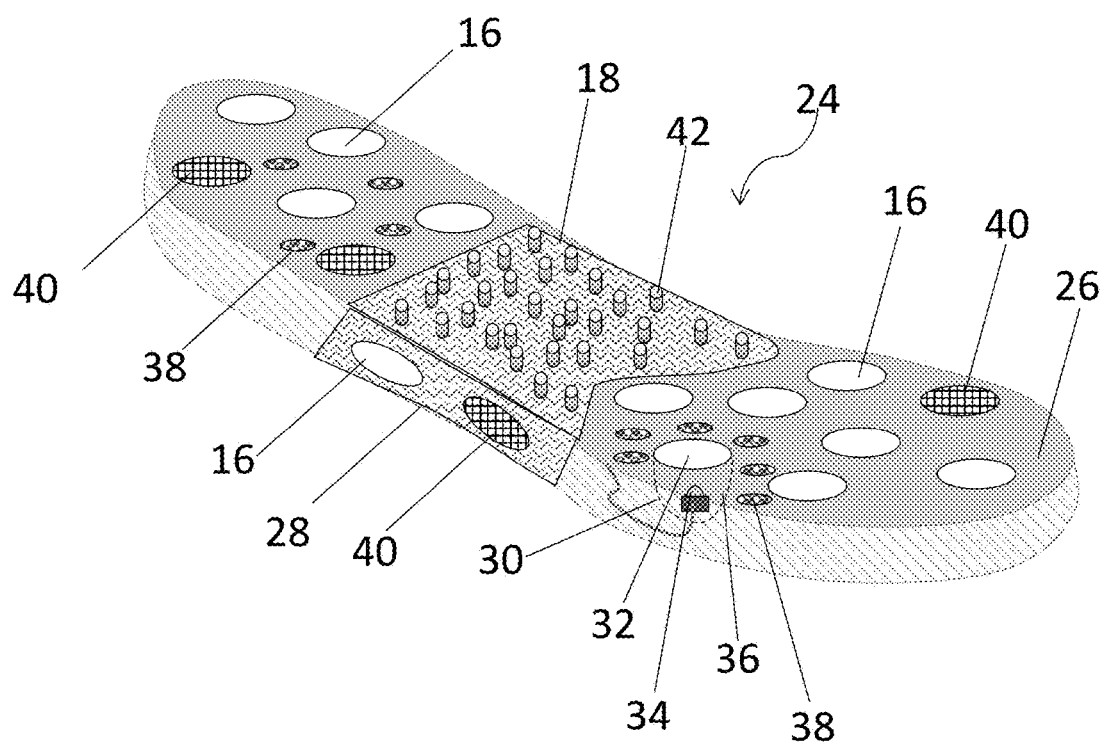
FIG. 3 shows an alternative insert for use with a UV footwear illuminator according to an embodiment of the present invention.

FIG. 3 shows an insert 24 for use with a UV footwear illuminator that is applicable with an article of footwear according to an embodiment of the present invention. In this embodiment, the insert 24 can include at least one UV radiation source 16 located on a top surface 26 of the insert and at least one UV radiation source 16 located on a side surface 28 of the insert 24. Although a bottom surface of the insert 24 is not shown, it is understood that the set of UV radiation sources 14 can also be located on this surface.

As shown in FIG. 3, each of the UV radiation sources 16 can be embedded within a domain 30 of the insert 24. For clarity, FIG. 3 only shows one domain 30, however, it is understood that each UV radiation source can have a domain 30 with the following elements. A top surface 32 of the domain can include a transparent window region through which the UV radiation emitted from a UV radiation emitter 34 passes there through. This transparent window region can be formed of any UV transparent material such as those materials described with respect to the transparent window region. An interior surface 36 of the domain 30 can be formed of a UV reflective material, such as a reflective fluoropolymer, such as PTFE, and/or the like, a UV reflective film using aluminum, a highly ultraviolet reflective expanded polytetrafluoroethylene (ePTFE) membrane (e.g., GORE® Diffuse Reflector Material), and/or the like.

The set of UV radiation sources 16 deployed with insert 24 can be configured in any desired pattern on the various surfaces of the insert that is deemed to provide optimal treatment of the article of footwear in which the insert is placed. In one embodiment, the set of UV radiation sources 16 can be located in clusters along the top surface 26 where a person's foot has the most contact to the interior of the footwear. For example, the set of UV radiation sources 16 can be disposed on the front and back portions of the insert 24.

The insert 24 of FIG. 3 can further include at least one footwear condition sensor 38 located therein. Each sensor 38 is configured to generate a condition signal representative of an operational parameter of the insert 24 and/or the article of footwear in which the insert is placed. Examples of sensors that can be deployed as footwear condition sensors 38 include, but are not limited to, a pressure sensor, a moisture sensor, a humidity sensor, a bacterial fluorescence sensor, a temperature sensor, a chemical sensor, a radiation sensor, a proximity sensor, and/or the like. The insert 24 is not limited to any one particular type of these sensors. Those skilled in the art will appreciate that the insert 24 can have footwear condition sensors 38 that include one type of sensor or various combinations of these sensors. Furthermore, the footwear condition sensors 38 can be deployed along with the UV radiation sources 16 in any desired configuration. For example, the footwear condition sensors 38 can be configured together or separate from the UV radiation sources 16. FIG. 3 shows one embodiment in which the footwear condition sensors 38 can be interspersed with the UV radiation sources 16.

The condition signal generated from the sensors 38 that is representative of an operational parameter of the insert 24 or the footwear that the insert is place therein will depend on the particular sensor that is deployed. For example, a pressure sensor can measure the foot pressure experienced by the insert 24 and/or the footwear. A humidity sensor and/or a moisture sensor can measure the humidity/moisture in the insert 24 and/or the footwear. A chemical sensor can detect a level of a particular chemical and/or an odor of that chemical that resides with the insert 24 and/or the footwear. A radiation sensor can detect a level of radiation (e.g., UV, visible, infrared, and/or the like) that is present in the insert 24 and/or the footwear. A proximity sensor can determine the proximity of the foot surface of the wearer of the footwear to the insert 24.

FIG. 3 shows that the insert 24 can further include at least one footwear treatment source 40. As used herein, a footwear treatment source 40 is any source that can provide a modality for effectuating footwear treatment to an article of footwear. The footwear treatment source 40 can include, but is not limited to, a visible source (e.g., a LED), an infrared source, a heating source (e.g., an electrical heating pad), a vibrational source, a medical treatment source (e.g., ultrasound source, electrical pulse stimulation source), and a chemical treatment source. In one embodiment, the visible source, infrared source, and/or heating source can be used to work in conjunction with the UV radiation sources 16 to provide footwear treatment (e.g., sanitization, disinfection, and sterilization for removing the presence of bacteria and viruses), while the vibrational source and the medical treatment source can provide a medical treatment for a foot placed on the insert 24 such as a massage, pulse stimulation and/or the like, and the chemical treatment source can release certain antibacterial chemicals to treat the insert, footwear and/or a foot placed therein.

Those skilled in the art will appreciate that the insert 24 can include only one type of footwear treatment source 40 or more than one type of the footwear treatment sources or various combinations of these treatment sources. Furthermore, the footwear treatment sources 40 can be deployed along with the UV radiation sources 16 and the footwear condition sensors 38 in any desired configuration. For example, the footwear treatment sources 40 can be configured together or separate from the UV radiation sources 16 and the footwear condition sensors 38. FIG. 3 shows one embodiment in which the footwear treatment sources 40 can be interspersed with the UV radiation sources 16 and the footwear condition sensors 38.

FIG. 3 shows that the insert 24 can further include a wave guiding structure 18 that is configured to direct and/or deliver UV radiation that is emitted from the UV radiation sources 16 to a particular location/area, along the insert 24, and in a particular direction and pattern that effectuates footwear treatment of the insert, the article of footwear that the insert is placed in, and foot of the wear of the footwear. As shown in FIG. 3, a set of diffusive elements 42 can be used in conjunction with the wave guiding structure 18 to distribute the UV radiation along the insert 24, article of footwear and a foot that is placed on the insert. The set of diffusive elements 42 can be configured to distribute the UV radiation in a uniform pattern and/or in a non-uniform pattern. As used herein, diffusive elements are any structure that facilitates scattering and dispersal of the UV radiation that is emitted from a UV radiation source 16. The diffusive elements 42 in FIG. 3 are illustrated in the form of small cylindrical-shaped knobs, however, other shapes and sizes are within the scope of the various embodiments of the present invention. In one embodiment, the diffusive elements 42 can be formed from material that includes an ultraviolet transparent material, such as a fluoropolymer material, fused silica, and/or the like. Other examples of materials of diffusive elements 42 that are suitable for use in FIG. 3 can include, but are not limited to, an ultraviolet reflective expanded polytetrafluoroethylene (ePTFE) membrane (e.g., GORE® Diffuse Reflector Material), and/or the like. Although it is not shown in FIG. 3, the set of diffusive elements 24 can be separated from the interior of the article of footwear by a UV transparent film, such as a fluoropolymer film.

Figure 4:
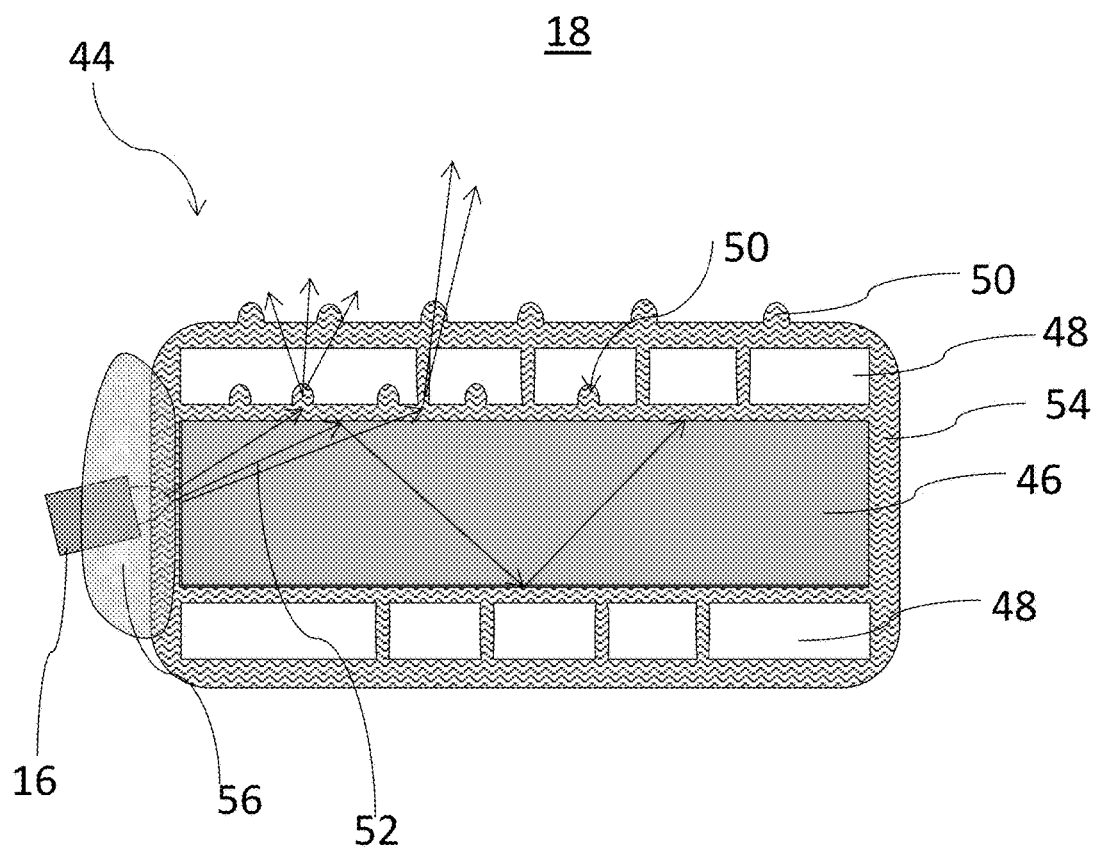
FIG. 4 shows a cross-sectional view of a wave guiding structure having a multilayer structure that is suitable for use with any of the various embodiments described herein.

FIG. 4 shows a cross-sectional view of a wave guiding structure 18 that may be used with any of the various embodiments described herein. In FIG. 4, the wave guiding structure 18 is illustrated as a multilayer structure 44. As shown in FIG. 4, the multilayer structure 44 can include a radiation guiding layer 46. In one embodiment, the radiation guiding layer 46 can include a UV transparent fluid. In this case, the fluid has a transparency at least similar (e.g., within ten percent) to the transparency of purified water for light wavelengths in the range of 240 nanometers to 360 nanometers. In an embodiment, the liquid in the layer 46 is purified water as defined by the U.S. Food and Drug Administration. Examples of other materials that can act as the radiation guiding layer 46 include but are not limited to ultraviolet transparent materials such as potable water, anodized aluminum oxide, and/or the like. Methods of forming radiation guiding layers are described in U.S. Provisional Application No. 62/050,126 and U.S. Provisional Application No. 62/050,127.

The radiation guiding layer 46 of FIG. 4 is disposed between refractory layers 48. As shown in FIG. 4, the refractory layers 48 can include pillars, however, it is possible to have a refractory layer including no pillars. In one embodiment, the refractory layers 48 can include low refractory materials such as, but not limited to, a gas (e.g., ambient air), and/or the like. As used herein, low refractory materials means any material having a refractive index at most ninety percent of the refractive index of the material forming adjacent layer(s) in a structure. For example, the material can have a refractive index in a range of 1 to 1.2.

Refractory layers 48 can include diffusive protrusions 50 to direct UV radiation 52 emitted from a UV radiation source 16 that is coupled to the multilayer structure 44. Note that the amount of diffusive protrusions 50 per refractory segment and/or layer can vary depending on the direction and pattern of the UV radiation that is desired, as well as the size and length of the segments and/or layers. As shown in FIG. 4, the top refractory layer 48 is configured with diffusive protrusions 50, with more protrusions in the segments that are closer to the UV radiation source 16, and less the further away the segments are from the radiation source.

An encapsulation layer 54 encapsulates the radiation guiding layer 46 and the refractory layers 48. As shown in FIG. 4, the encapsulation layer 54 can separate the radiation guiding layer 46 from the refractory layers 48. The encapsulation layer 54 can also form pillars present in the refractory layers 48. FIG. 4 shows that the encapsulation layer 54 can be shaped with diffusive protrusions 50 to facilitate the desired direction and pattern of the UV radiation 52 emitted from the UV radiation source 16 via the radiation guiding layer 46. The encapsulation layer 54 can include any of the aforementioned UV transparent materials, such as a fluoropolymer-based material.

FIG. 4 shows that in one embodiment the UV radiation source 16 can be coupled to the encapsulation layer 54 of the multilayer structure 44. In one embodiment, the UV radiation source 16 can be secured to the encapsulation layer 54 by placing the source in a highly adhesive UV transparent material 56 such as such as EFEP, a similar fluoropolymer, and/or the like, and fused to the encapsulation layer 54. In one embodiment, the fusion of the UV radiation source 16 to the encapsulation layer 54 can be performed at temperatures on the order of approximately 180 to approximately 200 degrees Celsius. The various embodiments of present invention are not meant to be limited to fusing a UV radiation source 16 to the radiation guiding layer and those skilled in the art will appreciate that other approaches that can optically couple these elements exist.

Figure 5:
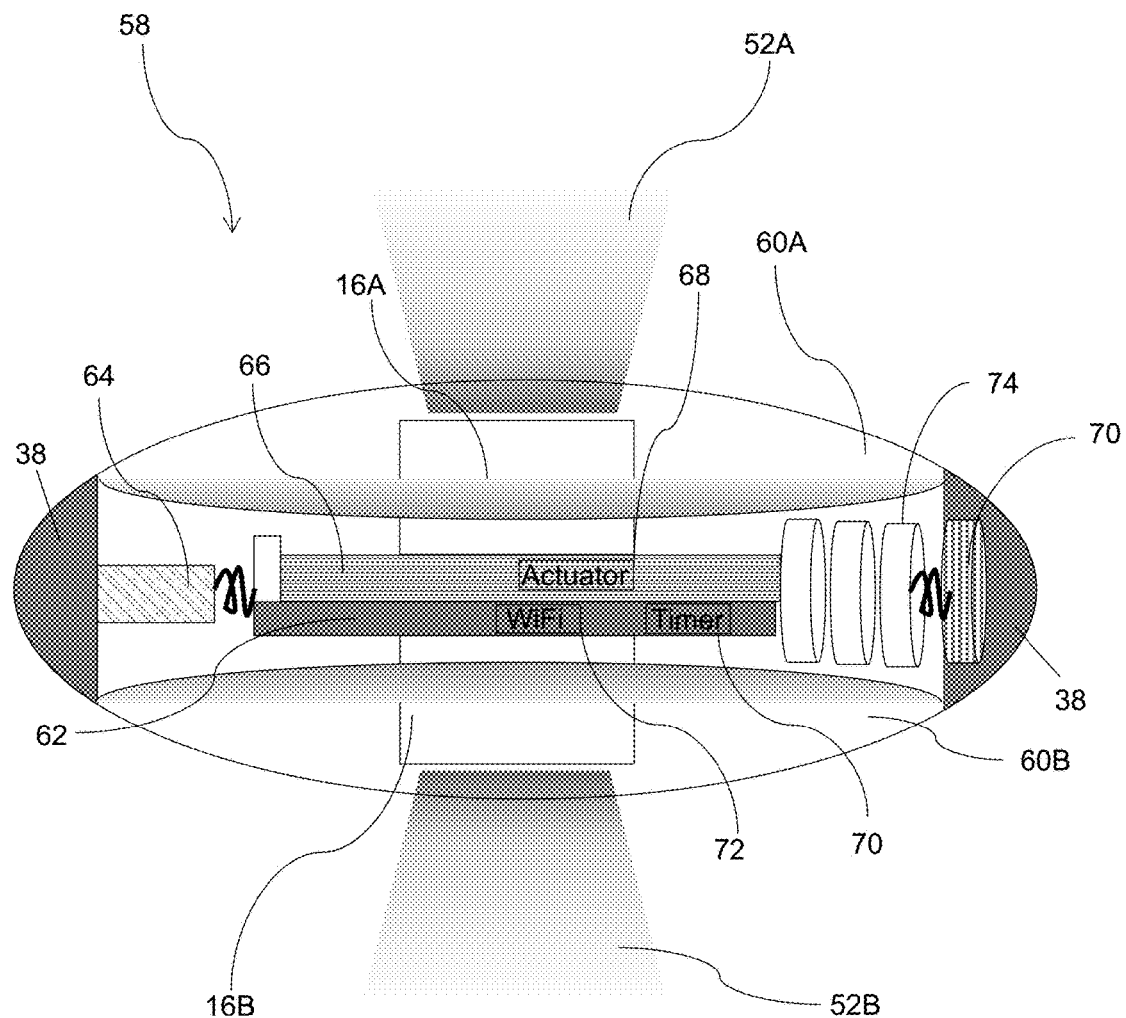
FIG. 5 shows a more detailed view of a portion of a UV radiation source that can be configured with a UV footwear illuminator described herein to form a UV footwear treatment system according to an embodiment of the present invention.

FIG. 5 shows a more detailed view of a portion of a UV radiation source 16 that can be configured with a UV footwear illuminator described herein to form a UV footwear treatment system 58 according to one embodiment of the present invention. As shown in FIG. 5, the UV footwear treatment system 58 can include a set of UV radiation sources 16A, 16B located adjacent to a respective UV transparent window region 60A, and 60B. In operation, the UV radiation source 16A emits UV radiation 52A through UV transparent window region 60A, while UV radiation source 16B emits UV radiation 52B through UV transparent window region 60B. Although not shown in FIG. 5, UV radiation 52A and 52B can be directed from UV transparent window region 60A and 60B, respectively, through a surface of the insert and towards a specific portion thereof, and/or a specific portion of the article of footwear, and/or a foot placed inside the footwear via a wave guiding structure and/or diffusive elements if utilized. Any one of the aforementioned examples of UV radiation sources can be used for UV radiation sources 16A and 16B. Likewise, any one of the aforementioned UV transparent materials can be used for UV transparent window regions 60A and 60B.

The UV footwear treatment system 58 of FIG. 5 can further include a control unit 66 to manage operation of the UV radiation sources 16A and 16B. In one embodiment, the control unit 66 can control at least one of a plurality of predetermined UV radiation characteristics associated with the UV radiation 52A and 52B emitted from the UV radiation sources 16A and 16B. The predetermined UV radiation characteristics that can be controlled by the control unit 66 can include wavelengths, intensities, and durations and/or the like. In one embodiment, the control unit 66 can control the wavelength of UV radiation and intensity spatially over an insert and/or the article of footwear in which the UV footwear treatment system 58 can be used. As an example, control unit 66 can control UV radiation source 16A to operate at a target wavelength and intensity for a duration that is designed for the disinfection of bacteria and/or viruses within an article of footwear. During this time, the control unit 66 can control UV radiation source 16B to operate at a different target wavelength and intensity for a specified duration that is designed for the medical treatment of the skin of a foot that is to be placed in the footwear. Those skilled in the art will readily appreciate that there are many possibilities in how the control unit 66 can control the UV radiation sources 16A and 16B.

Control unit 66 can also receive condition signals representative of certain operational parameters of the insert and/or the article of footwear in which the insert is placed from a footwear condition sensor 38 located at each end of the structure. As shown in FIG. 5, the footwear condition sensors 38 can be placed proximate the UV radiation sources 16A and 16B and the UV transparent window regions 60A and 60B. In one embodiment, the footwear condition sensors 38 can be placed between the respective UV radiation sources and UV transparent window regions. Any one of the aforementioned footwear condition sensors 38 is suitable for use with the UV footwear treatment system 58 illustrated in FIG. 5. In operation, the control unit 66 can receive the condition signals from the footwear condition sensors 38 and turn on or off the UV radiation sources dependent upon the detected conditions via an actuator 68. Likewise, the control unit 66 can adjust one or more of the UV radiation characteristics based on the detected conditions. In one embodiment, a footwear condition sensor 38 can detect a motion condition signal, which the control unit 66 uses as an input, and turn on or off the set of UV radiation sources 16A and 16B. Similarly, the control unit 66 can use the motion condition signal to adjust the intensity, the wavelength, the duration and or the pattern of the UV radiation 52A and 52B emitted from the UV radiation sources 16A and 16B, respectively.

As an example, the motion sensed at the footwear condition sensors 38 can indicate the pressure of a foot, vibration during walking, and/or the like, which is provided to the control unit 66 in the form of a condition signal which it uses to control the UV radiation sources. It is understood that although the above examples describe a motion sensed by the footwear condition sensors 38, motion is not necessary for the control unit to manage the UV radiation sources 16A and 16B. For example, in another embodiment, a capacitive touch footwear condition sensor 38 that does not rely on motion can be used to provide a signal to the control unit 66 to turn on or off the set of UV radiation sources. In another example, where a footwear condition sensor 38 takes the form of a pressure sensor, the control unit 66 can use a detected pressure signal for determining the presence of a foot. In this manner, the control unit 66 can cause the UV radiation sources 16A and 16B to switch from radiating in the UV-C range, which is optimal for germicidal (e.g., disinfection) purposes, to radiating in the UV-B range, which is optimal for the medical treatment of the foot.

Although not shown in FIG. 5, the control unit 66 can receive the condition signals from the footwear condition sensors 38 to control the operation of any footwear treatment sources 40 that may be deployed by the UV footwear treatment system 58. As mentioned before, the footwear treatment source 40 can include, but is not limited to, visible sources, infrared sources, heating sources, vibrational sources, medical treatment sources, and chemical treatment sources.

The control unit 66 can include a timer 70 with switches and/or the like to manage the duration that the UV radiation sources 16A and 16B are on for a particular treatment. For example, the control unit 66 operating in conjunction with the timer 70 can manage the amount of time that the UV radiation sources 16A and 16B radiate in the UV-C range versus the UV-B range. Similarly, the control unit 66 and the timer 70 can be used to control the duration of the operation of a footwear treatment source. The duration and frequency treatment that the UV radiation sources 16A and 16B and/or footwear treatment sources are utilized can depend on detected condition signals as well as any other predetermined footwear treatment factors such as the length that a particular article of footwear has been worn, following a set predefined treatment schedule.

The control unit 66 can also include a wireless transmitter and receiver 72 that is configured to communicate with a remote location via WiFi, BLUETOOTH, and/or the like. As used herein, a remote location is a location that is apart from the UV footwear treatment system 58, the insert and the footwear used therewith. For example, a remote computer can be used to transmit operational instructions to the wireless transmitter and receiver 72. The operational instruction can be used to program functions performed and managed by the control unit 66. In another embodiment, the wireless transmitter and receiver 72 can transmit footwear treatment results, data from the various footwear condition sensors to the remote computer, to facilitate maintenance and diagnostic operations on the UV footwear treatment system 58, etc.

The UV footwear treatment system 58 of FIG. 5, can further include a power source 74 that is configured to power each of the UV radiation sources 16A and 16B, the control unit 66 and the footwear condition sensors 38. In one embodiment, the power source 74 can take the form of one or more batteries. As shown in FIG. 5, a threading 76 can be used to provide access to the power source 74. In particular, the threading 76 allows an end of the UV footwear treatment system 58 to be removed. The threading 76 can provide a watertight seal between that particular end and the remaining portion of the UV footwear treatment system 58. Although FIG. 5 shows threading 76 for removably securing an end of the UV footwear treatment system 58, it is understood that any form of connection that forms a watertight seal, such as a gasket, and/or the like, can be utilized to secure the end to the remaining portion of the UV footwear treatment system 58. Furthermore, although a threading 76 is not shown at the opposite end, it is understood that a similar connection can be provided at this particular region of the UV footwear treatment system 58.

In addition to access and removal of the power source 74 the threading 76 allows for insertion and removal of one or more other components located in the UV footwear treatment system 58. For example, in one embodiment, the end coupled to threading 76 can be removed to replace the set of batteries used for powering the set of UV radiation sources 16A and 16B, the control unit 66, the footwear condition sensors 38, and any other components within the UV footwear treatment system 58. Although the power source 74 shown in FIG. 5 takes the form of batteries, it is understood that the UV footwear treatment system 58 can include other power supply components. For example, the power supply 74 can include a vibration power generator 62, which can generate power based on magnetic inducted oscillations or stresses developed on a piezoelectric crystal 64. In another embodiment, the power source 74 can include a super capacitor that is rechargeable. Other power components that are suitable for use as the power source 74 for the UV footwear treatment system 58 include a mechanical energy to electrical energy converter such as a piezoelectric crystal. The various embodiments of the present invention are not limited to using only one particular power supply modality. For example, a vibration power generator 62 can be used to generate power while a set of batteries 74 can be used to store the power generated from the vibration power generator 62.

In another embodiment, the power source 74 can be a rechargeable device. For example, a vibration power generator can be configured with rechargeable componentry. In another example, a wireless charging system can be used to charge the vibration power generator 62 from an electromagnetic signal. In yet another example, a charge can be provided by the use of a piezoelectric crystal that functions according to mechanical pressure. The type of power supply and the particular footwear treatment that is performed are factors that can determine how often a recharging operation is needed. For example, a typical LED, operating at 20 mill amperes (mA), with a coin battery rated 225 milli-ampere hour (mAH), can operate in a continuous mode for about 10 hours. For a typical LED, operating at 20 mA, with a coin battery rated 225 mAH, the LED can operate in a continuous mode for about 10 hours. A typical disinfection treatment session may last on the order of 10 minutes, thus resulting in approximately 60 disinfection sessions for the UV footwear treatment system 58 before the battery would need to be recharged or changed. For an extended life in this scenario, two or more coin batteries can be employed within the UV footwear treatment system 58.

The UV footwear treatment system 58 of FIG. 5 is shown having a prolate spheroid shape (e.g., football) with ends connected by elongated sides. In one embodiment, the UV footwear treatment system 58 with the prolate spheroid shape can have at most a volume of approximately 75 cm$^3$. Although the UV footwear treatment system 58 is shown as a prolate spheroid shape, those skilled in the art will appreciate that the prolate spheroid shape is only illustrative and that the UV footwear treatment system 58 can take the form of any shape.

Figure 7:
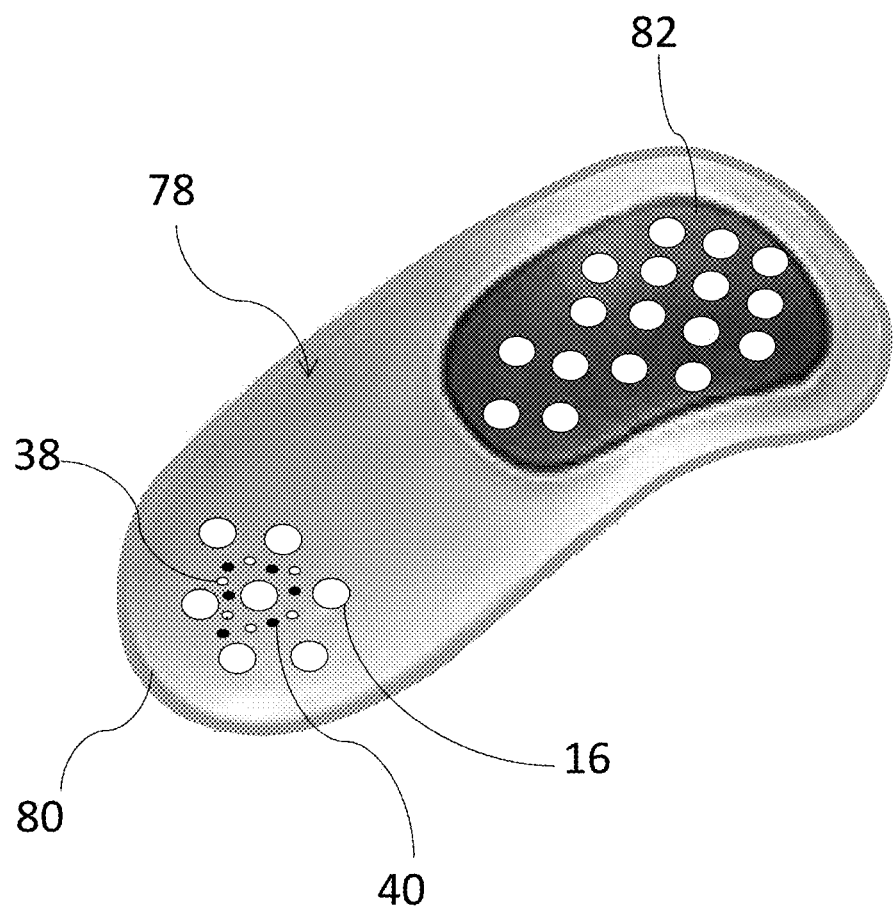
FIG. 7 shows a UV orthotic illuminator according to an embodiment of the present invention.

FIG. 7 shows a UV footwear illuminator used as an orthotic for placement into an article of footwear that can alleviate various foot ailments such as arch pain, plantar fasciitis, heel spurs, and the like. In particular, FIG. 7 shows a UV orthotic illuminator 78 according to one embodiment of the present invention. In this embodiment, the UV orthotic illuminator 78 can include UV radiation sources 16, footwear condition sensors 38 and footwear treatment sources 40. In FIG. 7, the UV radiation sources 16, the footwear condition sensor 38 and the footwear treatment sources 40 are interspersed with each other in a heel portion 80 of the UV orthotic illuminator 78. Those skilled in the art will appreciate that other patterns of placement of the UV radiation sources 16, the footwear condition sensors 38 and the footwear treatment sources 40 in the UV orthotic illuminator 78 are possible. For example, the UV radiation sources 16, the footwear condition sensors 38 and the footwear treatment sources 40 can be placed in a metatarsal pad section 82 of the UV orthotic illuminator 78. Furthermore, it may be desirable to have the UV radiation sources 16, the footwear condition sensors 38 and the footwear treatment sources 40 separate and not interspersed with each other.

Also, the UV orthotic illuminator 78 can utilize different combinations of the sources. For example, the heel portion 80 may only use footwear treatment sources 40 that treat certain foot ailments. Those skilled in the art will appreciate many combinations are possible. Although the UV orthotic illuminator 78 illustrated in FIG. 7 does not disclose the use of a wave guiding structure 18 it may be configured for use with the UV radiation sources 16. Furthermore, the UV orthotic illuminator 78 may also be configured as a UV footwear treatment system to include a control unit 66 and various other components (e.g., electronics and power supply) described with reference to FIG. 5.

Figure 8A:
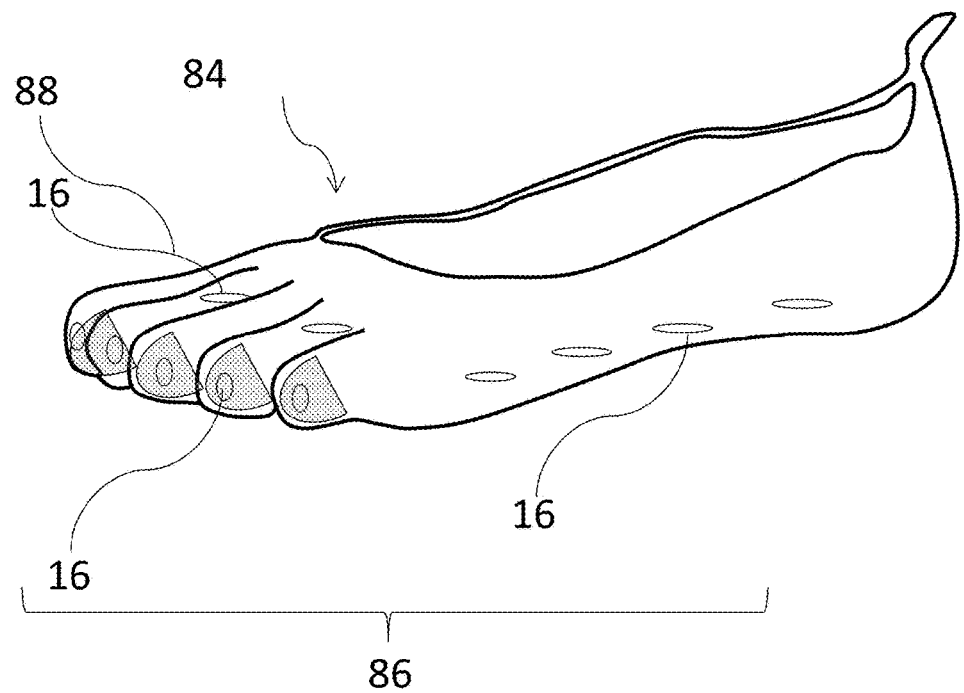
FIGS. 8A-8B show an article of footwear such as a toe shoe having a UV illuminator according to an embodiment of the present invention.
Figure 8B:
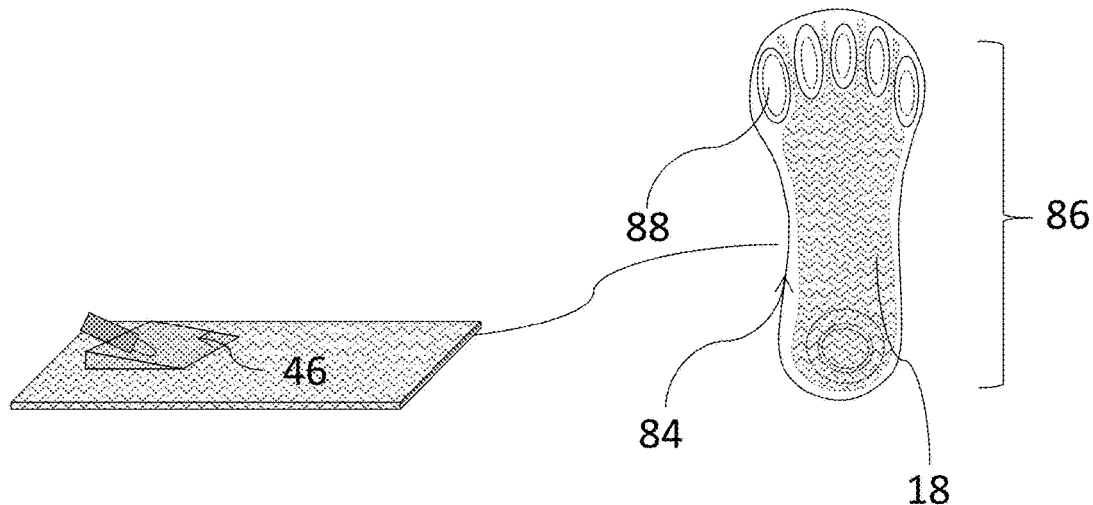

FIGS. 8A-8B show an article of footwear such as a toe shoe 84 having a toe shoe UV illuminator 86 according to one embodiment of the present invention. The toe shoe UV illuminator 86 can include UV radiation sources 16 located in different portions of the toe shoe 84. As shown in FIG. 8A, the toe shoe UV illuminator 86 can have UV radiation sources 16 located in a toe portion 88 of the toe shoe 84 including at the toes and the top portion of the toe portion 88. FIG. 8B shows that the toe shoe UV illuminator 86 can also include a wave guiding structure 18 that directs UV radiation to the toe portion 88 of the toe shoe 84. In one embodiment, the wave guiding structure can take the form of a multi-layer structure having a radiation guiding layer 46 like that illustrated in FIG. 4. In this manner, UV radiation can be guided to each toe of the toe portion 88 by the radiation guiding layer 46 of the wave guiding structure 18.

Those skilled in the art will appreciate that the toe shoe UV illuminator 86 can be configured in a different manner than the embodiment illustrated in FIG. 8. For example, the toe shoe UV illuminator 86 can be implemented with footwear condition sensors 38 and/or footwear treatment sources 40. Furthermore, the toe shoe UV illuminator 86 may be configured as a UV footwear treatment system to include a control unit 66 with the other components (e.g., electronics and power supply) described with reference to FIG. 5.

Figure 9:
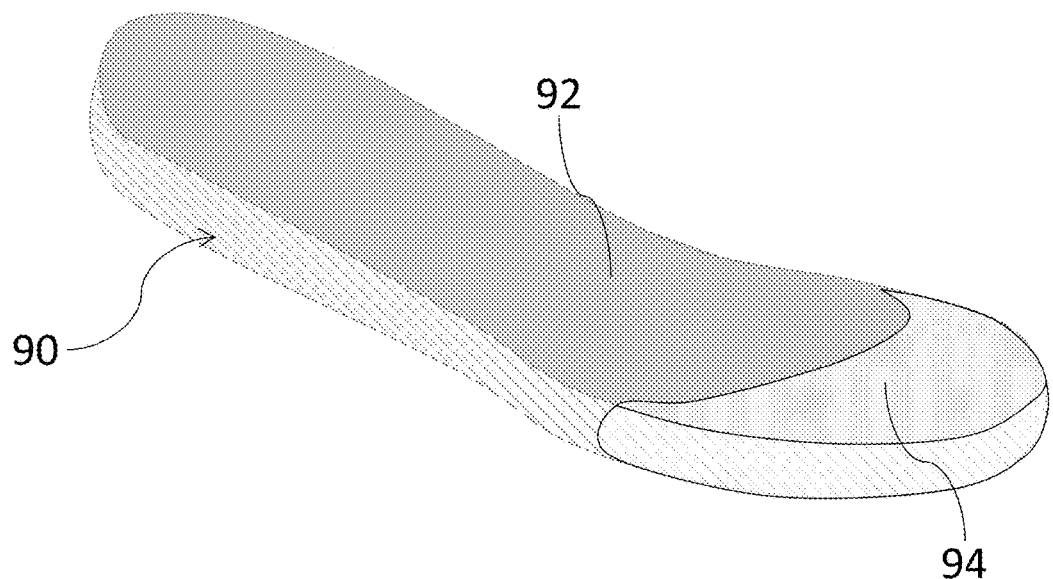
FIG. 9 shows a UV footwear illuminator that can provide an uniform illumination of UV radiation according to an embodiment of the present invention.

FIG. 9 shows a UV footwear illuminator 90 according to another embodiment of the present invention. The UV footwear illuminator 90 of FIG. 9 includes an insert 92 having a toe region 94 that is configured to provide a uniform illumination of UV radiation. In one embodiment, the toe region 94 can include partially transparent, partially reflective layers, wave guiding layers, reflective layers, and/or diffusive elements that are arranged to uniformly distribute the UV radiation from UV radiation sources. Further details of these layers are described in U.S. patent application Ser. No. 14/478,266. In this embodiment, while not shown for clarity, ultraviolet sources can be configured such that ultraviolet illumination enters the toe region 94. For example, ultraviolet sources can be placed in proximity to the region 94, with a light guiding structure described herein used to guide and emit diffusive ultraviolet radiation within the toe region 94.

Those skilled in the art will appreciate that the other configurations for UV footwear illuminator 90 are possible. For example, the UV footwear illuminator 90 can be implemented with footwear condition sensors 38 and/or footwear treatment sources 40. Furthermore, the UV footwear illuminator 90 may be configured as a UV footwear treatment system to include a control unit 66 with the other components (e.g., electronics and power supply) described with reference to FIG. 5.

Figure 10:
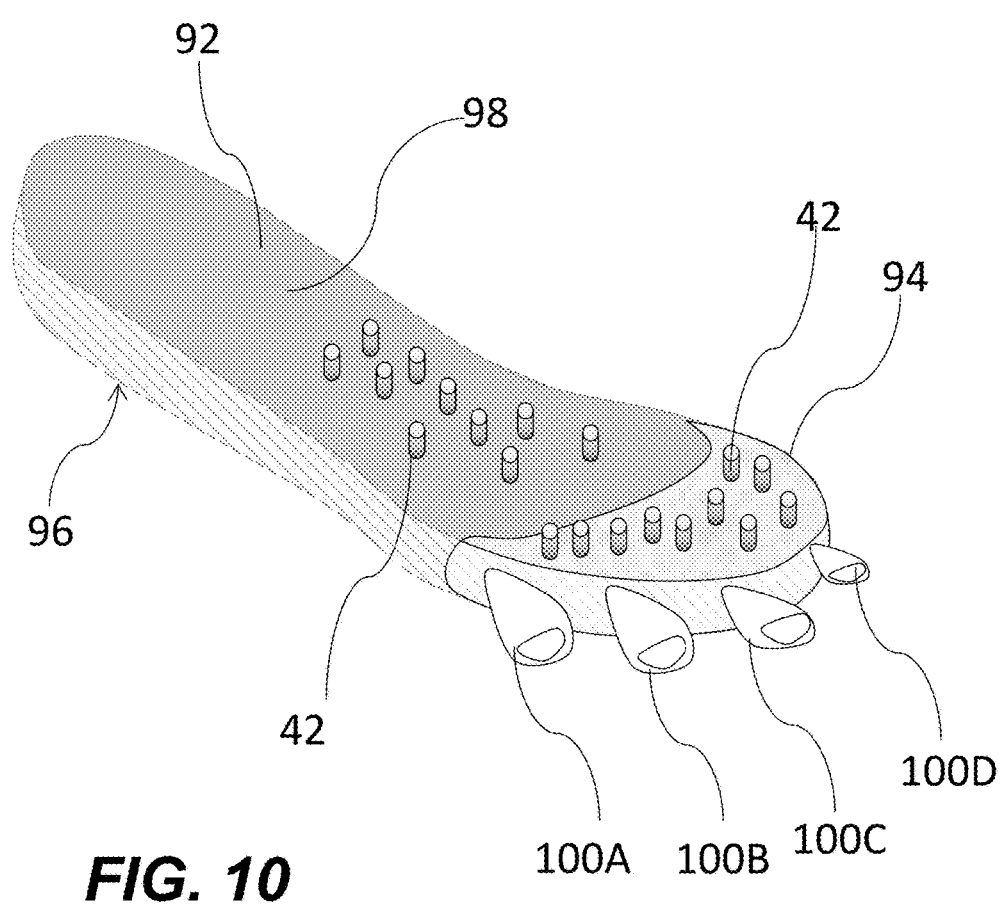
FIG. 10 shows a UV footwear illuminator that can have diffusive elements and toe protrusions according to an embodiment of the present invention.

FIG. 10 shows a UV footwear illuminator 96 according to another embodiment of the present invention. The UV footwear illuminator 96 of FIG. 10 includes an insert 92 having a toe region 94 and a main body 98 encompassing an arch portion and a heel portion of the footwear. As shown in FIG. 10, both the toe region 94 and the main body 98 of the insert 92 can have diffusive elements 42 positioned along different sections of each to direct and pattern UV radiation emitted from UV radiation sources, which can be located anywhere along the main body 98. In particular, the diffusive elements 42 can distribute the UV radiation along the insert 92, the article of footwear that the UV footwear illuminator 96 is deployed with and/or at a foot of a wearer that is placed on the insert. The set of diffusive elements 42 can be configured in various arrangements along the main body 98 and/or the toe region 94 to distribute the UV radiation in a uniform pattern and/or in a non-uniform pattern. As discussed with regard to FIG. 3, the diffusive elements 42 can be formed from the any of the aforementioned materials and take the form of various shapes and sizes in order to facilitate scattering and dispersal of the UV radiation in a desired arrangement.

The UV footwear illuminator 96 can further include toe protrusions 100 (e.g., 100A, 1008, 100C and 100D) to facilitate footwear treatment of the toe region 94. In one embodiment, the toe protrusions 100A-100D can be affixed to a periphery portion of the toe region 94 to apply a disinfection treatment thereof. The toe protrusions 100A-100D can include any combination of one or more: ultraviolet sources, light guiding structures, diffusive elements, and/or the like, as described herein. In one embodiment, the toe protrusions 100A-100D can perform a disinfection treatment of the toe region 94 by illuminating a corresponding portion of a shoe with ultraviolet light as described herein.

Those skilled in the art will appreciate that the UV footwear illuminator 96 can be configured in a different manner than the embodiment illustrated in FIG. 10. For example, the UV footwear illuminator 96 can be implemented with footwear condition sensors 38 and/or footwear treatment sources 40. Furthermore, the UV footwear illuminator 96 may be configured as a UV footwear treatment system to include a control unit 66 with the other components (e.g., electronics and power supply) described with reference to FIG. 5. Although the UV footwear illuminator 96 is shown in FIG. 10 with only four toe protrusions 100A-100D, it is understood that this is only illustrative and that the UV footwear illuminator 96 can include at least one protrusion or up to five protrusions.

The various embodiments of the present invention described herein are also suitable for use as shoe inserts or shoe trees that approximate the shape of a foot that is placed inside an article of footwear such as a shoe to preserve its shape, stop it from developing creases and thereby extend the life of the shoe. FIG. 11 shows a shoe tree 102 according to one embodiment of the present invention. The shoe tree 102 of FIG. 11 includes shoe insert bodies 104 (e.g., 104A and 104B) coupled together by springs 106. Each shoe insert body 104A and 104B can include UV radiation sources 16 and/or footwear treatment sources 40 for facilitating a footwear treatment of an article of footwear that the shoe tree 102 is placed in. The springs 106 are compressible and stretchable to enable the shoe insert body 104A to be vertically displaced with respect to the shoe insert body 1048. Although FIG. 11 shows three springs in use it is not meant to be limit the scope of this embodiment. Furthermore, those skilled in the art will recognize that the shoe tree 102 may be deployed with other compressive mechanisms.

Once the shoe body 104 (i.e., 104A and 104B) is placed in an article of footwear, then one can separate the shoe body 104A from the shoe body 1048 an amount that is sufficient to allow the shoe tree 102 to take the shape of the footwear. The desired tightness of incorporation of the shoe tree 102 in the footwear is user dependent. Once the shoe tree 102 is placed inside the article of footwear, an actuator 108 such as a switch and/or the like can be engaged to enable the shoe tree 102 to perform a footwear treatment. At least one of the shoe insert bodies 104A and 1048 can include an operation indicator 110 to include the status of the footwear treatment. For example, the operation indicator 110 can indicate whether a footwear treatment is currently in process, whether the treatment is finished, whether there was an issue associated with the treatment, etc. Once the footwear treatment is over, then the actuator 108 can be disengaged manually or automatically upon completion of the treatment or an issue therewith.

Although the shoe bodies 104A and 104B of shoe tree 102 are shown in FIG. 11 shown with UV radiation sources 16 and footwear treatment sources 40, this arrangement is not intended to be limited to such a configuration. For example, the footwear condition sensors 38 can be arranged with the UV radiation sources 16 and the footwear treatment sources 40. Also, the wave guiding structures 18 can be used in conjunction with the UV radiation sources 16 to distribute UV radiation to the footwear that the shoe tree 102 is placed in. Diffusive elements 42 can also be deployed with the shoe bodies 104A and 1048 to facilitate scattering and dispersal of the emitted UV radiation. The shoe bodies 104A and 104B can also include a control unit 66 and other components (e.g., electronics and power supply) as described with reference to FIG. 5 to facilitate the footwear treatment operations performed by the shoe tree 102 and enable it to function as a UV footwear treatment system.

Those skilled in the art will also appreciate that the shoe bodies 104A and 1048 can have only UV radiation sources 16 or only footwear treatment sources 40. Also, one shoe body 104 can have only UV radiation sources 16 while the other shoe body can have only footwear treatment sources 40. Similarly, the UV radiation sources 16 and the footwear treatment sources 40 can be arranged with each other on the shoe bodies in any direction and pattern as desired to effectuate a suitable treatment.

FIG. 12 shows a shoe tree 112 according to another embodiment of the present invention. In this embodiment, the shoe tree 112 is inflatable to take the shape of the footwear that it is placed. As shown in FIG. 12, the shoe tree 112 can include an inflatable main body 114 that is configured to take the shape of an article of footwear. The inflatable main body 114 includes a valve 116 that enables one to pump the main body so that the body inflates to take the shape of the footwear. The valve 116 enables the user to inflate the shoe tree 112 with enough air to obtain the desired tightness within the footwear. The shoe tree 112 of FIG. 12 further includes UV radiation sources 16 arranged along the main body 114.

Once the shoe tree 112 is placed inside the article of footwear, an actuator 108 such as a switch and/or the like located on the main body 114 can be engaged to enable the shoe tree 112 to perform a footwear treatment. The main body 114 of the shoe tree 112 can further include an operation indicator 110 to include the status of the footwear treatment. The operation indicator 110 can indicate items of information including, but not limited to, whether a footwear treatment is currently in process, whether the treatment is finished, whether there was an issue associated with the treatment, etc. Once the footwear treatment is over, then the actuator 108 can be disengaged manually or automatically upon completion of the treatment or an issue therewith.

FIG. 13 shows a shoe tree 118 according to another embodiment of the present invention. In this embodiment, the shoe tree 118 is also inflatable to take the shape of the footwear that it is placed like the shoe tree 112 of FIG. 12. In this embodiment, the main body 114 of the shoe tree 118 of FIG. 13 includes a wave guiding structure 18 that can have a radiation guiding layer as described herein and a set of diffusive elements 42 arranged along an upper portion 120 of the main body 114.

Those skilled in the art will appreciate that the shoes trees of FIGS. 12-13 can be arranged with many of the aforementioned components in one of a number of different combinations. For example, the UV radiation sources 16, the footwear treatment sources 40, the waveguide structure 18 and the diffusive elements can be configured with the shoe trees of FIGS. 12-13 all together, separate, or combinations thereof to obtain a desired direction and pattern of UV radiation that effectuates a footwear treatment. Similarly, it may be desirable to utilize one or more footwear condition sensors 38 with the shoe trees of FIGS. 12-13. Furthermore, the shoes trees of FIGS. 12-13 can also include a control unit 66 and electronics and power supply as described with reference to FIG. 5 to facilitate the footwear treatment operations performed by the shoe trees, and enable them to function as UV footwear treatment systems.

The various UV footwear illuminators, UV footwear treatment systems, articles of footwear and shoe trees described herein can employ materials that further facilitate the footwear and medical treatments. For example, the materials used for the various foot inserts of the UV footwear illuminators, the articles of footwear and the main bodies of the shoe trees can include photocatalytic layers, such as a titanium oxide ($TiO_2$) photocatalytic layer, a copper photocatalytic layer, a silver photocatalytic layer and/or the like, to improve the efficiency of a footwear treatment such as a disinfection operation. In one embodiment, a UV-$TiO_2$ photocatalytic layer is non-toxic and has a broad spectrum sterilizing ability, making it suitable for use with any one of the various embodiments of the present invention. Furthermore, the materials used for the various UV footwear illuminators, UV footwear treatment systems, articles of footwear and shoe trees described herein can include materials that are waterproof, water resistant, and tear resistant, such as one or more of the materials described herein.

It is understood, that during some footwear treatment operations it may be desirable for a user of any of the various embodiments of the present invention to avoid the UV radiation. For example, during a disinfection cycle where UV radiation sources are operating in a UV-C range, the footwear illuminators, footwear treatment systems, articles of footwear and shoe trees should probably be isolated from the user to avoid irradiating him or her with any UV light. One approach can include placing the footwear illuminators, footwear treatment systems, articles of footwear and shoe trees in a UV absorbing box. Once inside the box, then one of the footwear illuminators, footwear treatment systems, articles of footwear and shoe trees can be activated by switch after closing the UV absorbing box. A cover of such a UV absorbing box can have a visible indicator to provide status information on any footwear treatment operations being performed.

Figure 14:
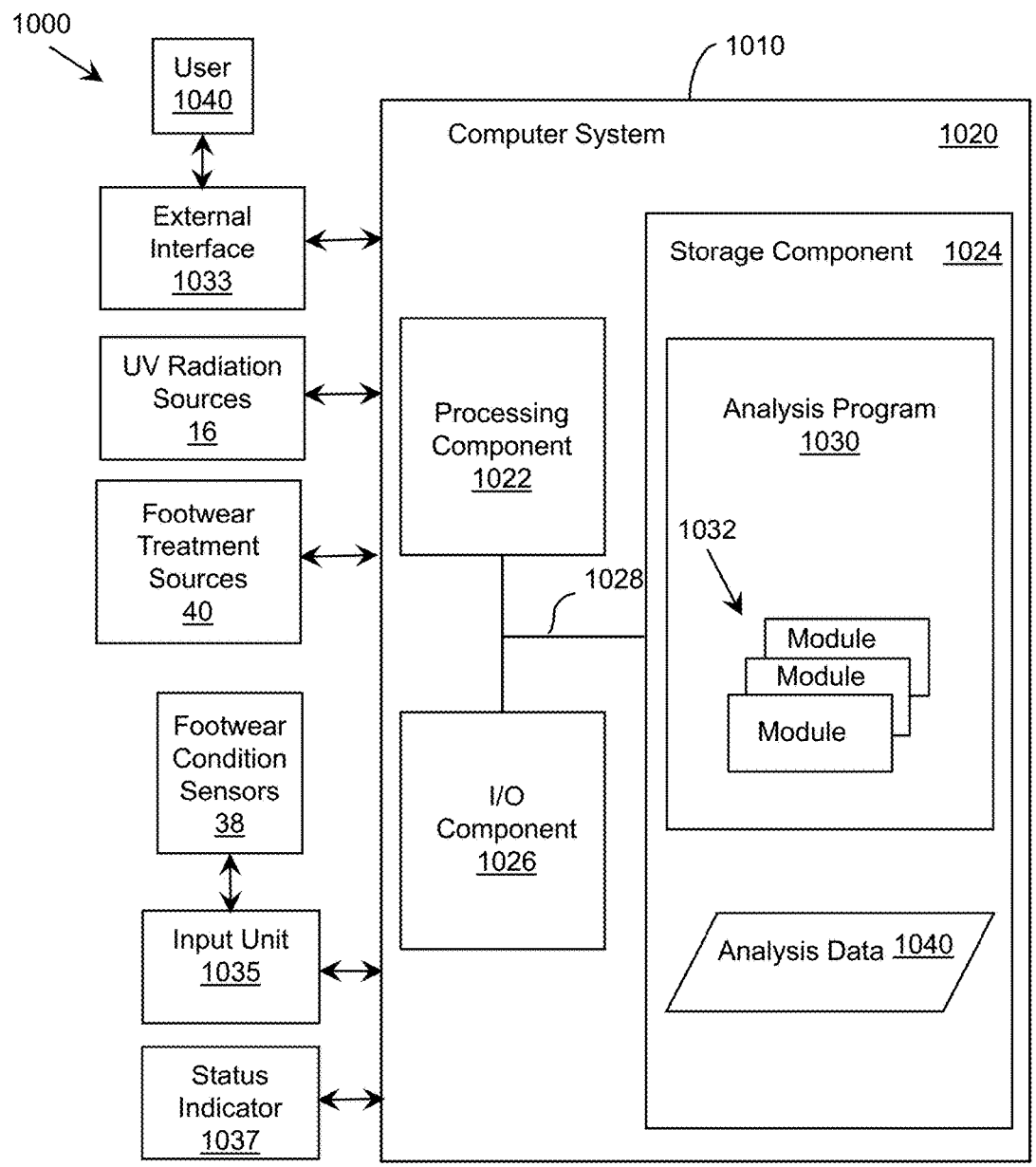
FIG. 14 shows an illustrative environment according to an embodiment.

FIG. 14 shows an illustrative system 1000 for implementing a UV footwear illuminator and a UV footwear treatment system described herein according to one embodiment. The system 1000 of FIG. 14 includes a monitoring and/or control system 1010, which is implemented as a computer system 1020 including an analysis program 1030, which makes the computer system 1020 operable to manage UV radiation sources 16, footwear condition sensors 38 and footwear treatment sources 40 by performing a process described herein. Portions of the system 1000 can be located within the UV footwear illuminators and UV footwear treatment systems as discussed herein. In particular, the analysis program 1030 can enable the computer system 1020 to operate the UV radiation sources 16 to generate and direct UV radiation through a UV transparent window and process data corresponding to one or more conditions of an article of footwear detected by one or more of the footwear conditions sensors 38 which is acquired by an input unit 1035. Similarly, the analysis program 1030 can enable the computer system 1020 to operate the footwear treatment sources 40 to perform one of the operations and process data corresponding to one or more conditions of the article of footwear detected by one or more of the footwear conditions sensors 38.

The computer system 1020 is shown including a processing component 1022 (e.g., one or more processors), a storage component 1024 (e.g., a storage hierarchy), an input/output (I/O) component 1026 (e.g., one or more I/O interfaces and/or devices), and a communications pathway 1028. In general, the processing component 1022 executes program code, such as the analysis program 1030, which is at least partially fixed in storage component 1024. While executing program code, the processing component 1022 can process data, which can result in reading and/or writing transformed data from/to the storage component 1024 and/or the I/O component 1026 for further processing. The pathway 1028 provides a communications link between each of the components in the computer system 1020. The I/O component 1026 can comprise one or more human I/O devices, which enable a human user 1040 to interact with the computer system 1020 and/or one or more communications devices to enable a system user 1040 to communicate with the computer system 1020 using any type of communications link via an external interface 1033. To this extent, the analysis program 1030 can manage a set of interfaces (e.g., graphical user interface(s), application program interface, and/or the like) that enable human and/or system users 1040 to interact with the analysis program 1030. Furthermore, the analysis program 1030 can manage (e.g., store, retrieve, create, manipulate, organize, present, etc.) the data, such as analysis data 1040, using any solution.

In any event, the computer system 1020 can comprise one or more general purpose computing articles of manufacture (e.g., computing devices) capable of executing program code, such as the analysis program 1030, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the analysis program 1030 can be embodied as any combination of system software and/or application software.

Furthermore, the analysis program 1030 can be implemented using a set of modules 1032. In this case, a module 1032 can enable the computer system 1020 to perform a set of tasks used by the analysis program 1030, and can be separately developed and/or implemented apart from other portions of the analysis program 1030. As used herein, the term "component" means any configuration of hardware, with or without software, which implements the functionality described in conjunction therewith using any solution, while the term "module" means program code that enables a computer system 1020 to implement the actions described in conjunction therewith using any solution. When fixed in a storage component 1024 of a computer system 1020 that includes a processing component 1022, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 1020.

When the computer system 1020 comprises multiple computing devices, each computing device can have only a portion of the analysis program 1030 fixed thereon (e.g., one or more modules 1032). However, it is understood that the computer system 1020 and the analysis program 1030 are only representative of various possible equivalent computer systems that may perform a process described herein. To this extent, in other embodiments, the functionality provided by the computer system 1020 and the analysis program 1030 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 1020 includes multiple computing devices, the computing devices can communicate over any type of communications link. Furthermore, while performing a process described herein, the computer system 1020 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols. Furthermore, the computer system 1020 can be programmed via WiFi. In this embodiment, the computer system 1020 can provide reports to the user 1040 or one or more other computer systems via WiFi regarding any aspect to the illustrative environment 1000, including, but not limited to UV illumination of articles of footwear for footwear treatment. Similarly, the computer system 1020 can generate footwear treatment operation status information via a status indicator 1037.

While shown and described herein as a method and system for UV illumination of articles of footwear for footwear treatment, it is understood that aspects of the present invention further provide various alternative embodiments. For example, in one embodiment, the various embodiments of the present invention provide a computer program fixed in at least one computer-readable medium, which when executed, enables a computer system to disinfect an area using UV radiation. To this extent, the computer-readable medium includes program code, such as the analysis program 1030 (FIG. 14), which enables a computer system to implement some or all of a process described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; and/or the like.

In another embodiment, the various embodiments of the present invention provide a method of providing a copy of program code, such as the analysis program 1030 (FIG. 14), which enables a computer system to implement some or all of a process described herein. In this case, a computer system can process a copy of the program code to generate and transmit, for reception at a second, distinct location, a set of data signals that has one or more of its characteristics set and/or changed in such a manner as to encode a copy of the program code in the set of data signals. Similarly, an embodiment of the present invention provides a method of acquiring a copy of the program code, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the various embodiments of the present invention provide a method for UV illumination of articles of footwear for footwear treatment. In this case, the generating can include configuring a computer system, such as the computer system 1020 (FIG. 14), to implement the method for UV illumination of articles of footwear for footwear treatment. The configuring can include obtaining (e.g., creating, maintaining, purchasing, modifying, using, making available, etc.) one or more hardware components, with or without one or more software modules, and setting up the components and/or modules to implement a process described herein. To this extent, the configuring can include deploying one or more components to the computer system, which can comprise one or more of: (1) installing program code on a computing device; (2) adding one or more computing and/or I/O devices to the computer system; (3) incorporating and/or modifying the computer system to enable it to perform a process described herein; and/or the like.

The foregoing description of the various aspects of the present invention has been presented for purposes of illustration and description. It is not intended to be exhaustive or to limit the various embodiments of the present invention to the precise form disclosed, and obviously, many modifications and variations are possible. Such modifications and variations that may be apparent to an individual in the art are considered to fall within the scope of the various embodiments of the present invention.

What is claimed is:

1. An ultraviolet (UV) footwear illuminator, comprising:
an insert adapted for placement in an article of footwear;
at least one UV radiation source located in the insert configured to emit UV radiation in the footwear through a transparent window region formed in the insert;
a wave guiding structure located in the insert, wherein the wave guiding structure is configured to distribute the UV radiation from the at least one UV radiation source to a plurality of locations within the footwear, wherein the wave guiding structure comprises a multilayer structure having at least one UV transparent fluoropolymer layer disposed between a pair of segmented liquid layers, a plurality of diffusive protrusions disposed in at least one of the liquid layers, and an encapsulation layer that encapsulates the at least one UV transparent fluoropolymer layer, the pair of liquid layers and the plurality of diffusive protrusions;
a control unit configured to control at least one of a plurality of predetermined UV radiation characteristics associated with the radiation emitted from the at least one UV radiation source; and
a power supply configured to power the at least one UV radiation source and the control unit.

2. The UV footwear illuminator according to claim 1, wherein the insert comprises an insole for use in the footwear.

3. The UV footwear illuminator according to claim 1, further comprising an actuator configured to activate the at least one UV radiation source.

4. The UV footwear illuminator according to claim 1, further comprising at least one footwear condition sensor located in the insert, each sensor configured to generate a condition signal representative of an operational parameter of the insert and/or footwear.

5. The UV footwear illuminator according to claim 4, wherein each footwear condition sensor is selected from the group consisting of a pressure sensor, a moisture sensor, a humidity sensor, a bacterial fluorescent sensor, a temperature sensor, a chemical sensor, a radiation sensor, and a proximity sensor.

6. The UV footwear illuminator according to claim 4, wherein the control unit controls each predetermined UV radiation characteristic as a function of each condition signal generated from each footwear condition sensor.

7. The UV footwear illuminator according to claim 1, further comprising at least one footwear treatment source located in the insert, wherein the at least one footwear treatment source is selected from a group consisting of: a visible source, an infrared source, and a heating source.

8. The UV footwear illuminator according to claim 1, wherein the wave guiding structure comprises a plurality of diffusive elements coupled thereto that distribute UV radiation in a uniform pattern.

9. The UV footwear illuminator according to claim 1, wherein the wave guiding structure comprises a plurality of protrusions configured to direct the UV radiation to a toe portion of the footwear.

10. The UV footwear illuminator according to claim 1, further comprising at least one footwear treatment source located in the insert, wherein the at least one footwear treatment source is selected from a group consisting of: a vibrational source, an ultrasound source, an electrical pulse stimulation source, and a chemical treatment source.

11. The UV footwear illuminator according to claim 1, wherein each of the at least one UV radiation source is coupled to the wave guiding structure.

12. An ultraviolet (UV) footwear treatment system, comprising:
an insert adapted for placement in an article of footwear;
at least one UV radiation source enclosed in the insert configured to emit UV radiation in the footwear through a transparent window region formed in the insert; and
a wave guiding structure configured to distribute the UV radiation generated from the at least one UV radiation source throughout the footwear, wherein the wave guiding structure comprises a multilayer structure having at least one UV transparent fluoropolymer layer disposed between a pair of segmented liquid layers, a plurality of diffusive protrusions disposed in at least one of the liquid layers, and an encapsulation layer that encapsulates the at least one UV transparent fluoropolymer layer, the pair of liquid layers and the plurality of diffusive protrusions.

13. The UV footwear treatment system according to claim 12, further comprising:
at least one footwear condition sensor located in the insert, each sensor configured to generate a footwear condition signal representative of an operational condition; and
a control unit configured to receive the footwear condition signal from each footwear condition sensor and control at least one of a plurality of predetermined UV radiation characteristics associated with the radiation emitted from each UV radiation source as a function of the footwear condition signal.

14. The UV footwear treatment system according to claim 13, wherein the control unit comprises a wireless transmitter and receiver that is configured to transmit footwear treatment results to a remote location and receive operational instructions therefrom.

15. The UV footwear treatment system according to claim 13, further comprising at least one footwear treatment source enclosed within the insert controlled by the control unit, the at least one footwear treatment source comprising one of a visible source, an infrared source, a heating source, a vibrational source, a medical treatment source and a chemical treatment source.

16. The UV footwear treatment system according to claim 13, further comprising a power supply configured to power each UV radiation source and the control unit, the power supply comprising at least one of: a battery supply, a vibrational power generator, a capacitor, and a mechanical energy to electrical energy converter.

17. The UV footwear treatment system according to claim 13, further comprising an operation indicator that provides status information of any footwear treatment operation performed on the footwear.

18. An article of footwear, comprising:
an insole insert having at least one UV radiation source located therein configured to emit UV radiation in the footwear through a transparent window region;
a wave guiding structure configured to distribute the UV radiation generation from each UV radiation source throughout the footwear, wherein the wave guiding structure comprises a multilayer structure having at least one UV transparent fluoropolymer layer disposed between a pair of segmented liquid layers, a plurality of diffusive protrusions disposed in at least one of the liquid layers, and an encapsulation layer that encapsulates the at least one UV transparent fluoropolymer layer, the pair of liquid layers and the plurality of diffusive protrusions;

at least one footwear condition sensor located in the insert, each sensor configured to generate a footwear condition signal representative of an operational condition; and a control unit configured to control operation of the at least one UV radiation source and the at least one footwear condition sensor.

19. The article of footwear according to claim 18, wherein the wave guiding structure includes a plurality of diffusive elements coupled thereto that distribute the UV radiation throughout the footwear.

20. The article of footwear according to claim 18, further comprising a toe portion having at least one toe UV radiation source to emit UV radiation at the toes of a wearer of the footwear.

\* \* \* \* \*